United States Patent [19]

Cummins

[11] 4,245,629
[45] Jan. 20, 1981

[54] KNEE AND ELBOW JOINT PROTECTOR

[76] Inventor: Alfred B. Cummins, 552 Sears Library CWRU, Cleveland, Ohio 44106

[21] Appl. No.: 969,212

[22] Filed: Dec. 13, 1978

[51] Int. Cl.³ .......................... A61F 5/00; A61F 1/04
[52] U.S. Cl. ...................................... 128/80 C; 3/22; 2/22
[58] Field of Search ............... 128/80 R, 80 C, 80 F, 128/87 R, 88; 2/16, 22, 24; 3/22, 24, 26, 27

[56] References Cited

U.S. PATENT DOCUMENTS

| 552,143 | 12/1895 | Rankin | 128/80 F |
|---|---|---|---|
| 1,660,721 | 2/1928 | Schrag | 128/80 F |
| 2,632,440 | 3/1953 | Hauser et al. | 128/80 F |
| 2,959,168 | 11/1960 | Shook | 2/22 |
| 3,350,719 | 11/1967 | McClure, Jr. | 2/22 |
| 3,817,244 | 6/1974 | Taylor | 128/80 C |
| 3,902,482 | 9/1975 | Taylor | 128/80 F |
| 4,130,115 | 12/1978 | Taylor | 128/80 C |

FOREIGN PATENT DOCUMENTS 1011204  5/1977  Canada .................. 128/80 C

*Primary Examiner*—Robert W. Michell
*Assistant Examiner*—Arthur S. Rose
*Attorney, Agent, or Firm*—Baldwin, Egan, Walling & Fetzer

[57] ABSTRACT

This invention is an implement for (1) preventing injuries to human knees by absorbing and spreading an external blow and (2) orthopedic procedures for therapy and rehabilitation. The concept is a (A) floating rocker connection axis beside the leg joint, which connects to (B) substantially rigid tongues encased in (C) substantially rigid sleeves fitted to the limbs above and below the rocker connection, appropriately padded for comfortable fit and wrapped with conventional taping. As the leg bends the tongues slide randomly in respective sleeves and the rocker connection adjusts to the pulls and pushes of the tongues, floating with the limb joint's natural hinge. One embodiment employs multiple narrow tongues for differential sliding inside the sleeves for easier more flexible motion in non-contact service. The single wide tongues of a second embodiment, more rigid and restrictive, are for therapeutic locking of desired positions of limbs, and for contact sports where units on both sides of a joint are securely wrapped for impact and twists. The rocker connection and tongues component is used for all applications; the sleeve with curved outside surfaces is (A) directly fitted to arm limbs or (B) attached to a fitted curved wrap plate for leg applications. Reversing one side's direction of bend for units on each side of a limb joint locks the entire limb straight, in effect an "open air" cast. A simple adjustment in the rocker connection enables locking of the bent limb in any position up to 90 degrees. Hyperextension limb injuries can be prevented and excessive limb twisting is controlled, by the one-way bend limitation of each unit. For simplicity and brevity hereinafter, discussion will focus on the knee only, elbow references being implied.

6 Claims, 8 Drawing Figures

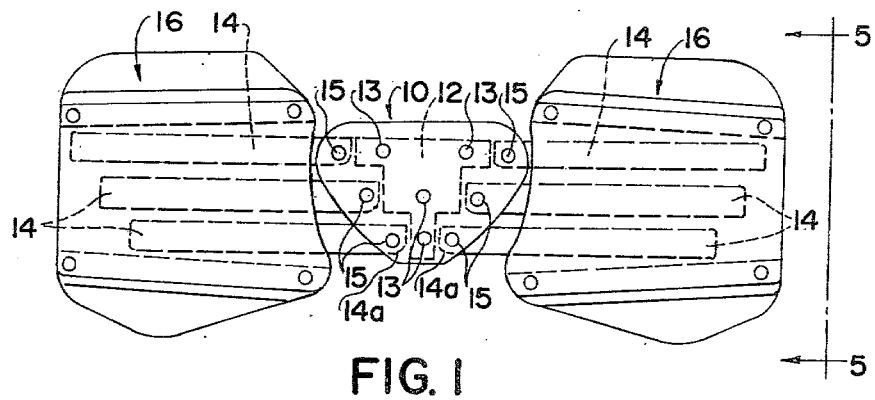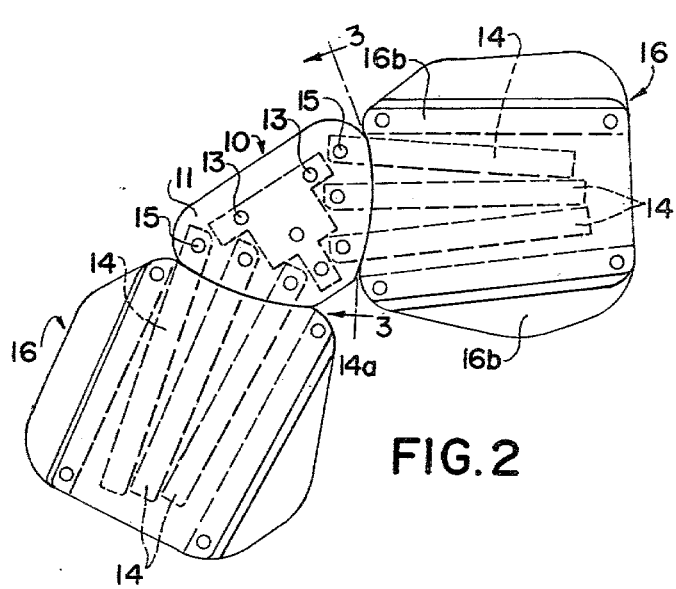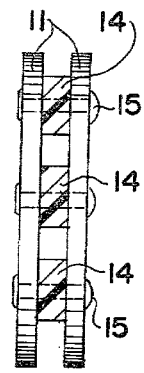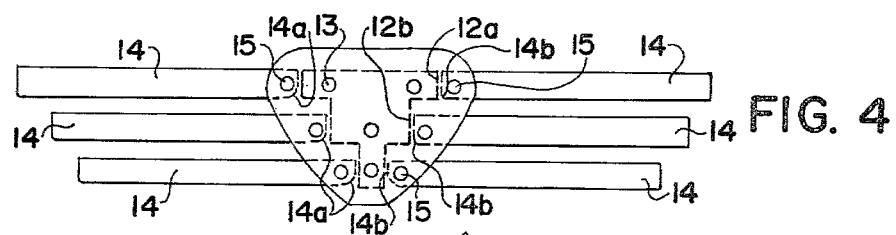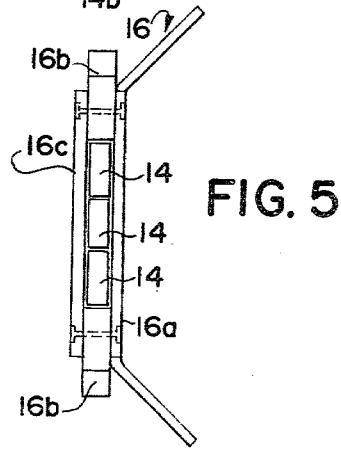

KNEE AND ELBOW JOINT PROTECTOR

BACKGROUND OF THE INVENTION

In very active contact sports, such as football, players often receive knee injuries from blows received in the course of the game. These blows are often delivered on one side or the other of the leg, for example, but such blows could also be received in the front of the leg. Both legs and arms suffer hyper-extensions at joints. These injuries often disable players for further participation in such games, and often are painful and take a long time to heal, frequently leaving limbs permanently impaired.

An object of this invention is to provide a protective support for the human knee joint. It provides a floating rocker connection member which is placed on at least one side of the knee joint with two linear rigid tongues, each pivotally connected in a spaced manner at one end inside the rocker connection member, one of these tongues being in position to extend along the leg immediately above the knee joint, respectively, and the other of the tongues being in position to extend along the leg immediately below the knee joint. A sleeve surrounds each tongue fastened to the adjacent limb by tapes or the like and sufficiently close to the associated tongue to permit free longitudinal movement of the tongue in the sleeve but preventing twisting of the tongue about its pivotal connection. The connection between the rocker connection member and the tongues is such that it permits substantially free bending of the knee joint for normal bending but prevents reverse bending of the knee joint almost entirely. The tongues, as described herein, have sufficient body and are tough enough to stand tremendous impact wherein the blow is spread along the length of the sleeve, tongue and rocker members and is safely absorbed by the limb muscles without dangerous injury to the joint.

Two embodiments of the invention are presented. The first of these is intended for general use in orthopedic procedures and in active sports for maximum limb flexibility and is shown as having three generally parallel tongues each pivotally connected to a central rocker connection member on an individual pivot, there being three of these guides in position to extend above the knee of the wearer and the other three on the opposite side extending down the leg of the wearer.

A second embodiment is also intended for both therapeutic applications and contact sports where very close, maximum rigidity fit to a limb is wanted. With the interfitting parts of this invention made to close dimensions, a snug fitting of maximum protection from a blow or push from in front is achieved. With one of these units on each side of a joint maximum shock absorption is achieved. One pair of tongues may be reversed in bending direction to achieve a rigid stiff leg, that is, an open air cast. In this manner, leg twisting is reduced or eliminated by proper attachment to the limb, respectively. This second embodiment will be used in regular football service and other contact sports, if the tongues and their surrounding sleeves are given a slight looseness for essential free sliding.

This invention, when constructed with one protector on each side of the joint and permitting substantially free bending of the joint in normal direction but preventing reverse bending of the joint, gives one-way flexibility. In standing position of the wearer, for example, the two guides extending in opposite directions from the knee joint become a column, unyielding to a hyper-extensive bend. This provides for: (1) resistance to a blow from the front; (2) distributes side blows to leg muscles; (3) preventing a severe twist of the leg joints; (4) cyclical restoration of the positioning of the systems components, and (5) when used for a temporary leg cast with the bending position reversed on opposite sides of the leg, to force the structures to work against each other, it becomes a rigid structure preventing knee joint action.

An object of the use of the present invention in active contact sports is to obviate damage to a player's knee joints by providing units constructed according to this invention firmly attached to the player's limbs above and below the joints, and so constructed and arranged that they give the player free use of his limbs in playing a game but resist, as shown by actual test, a blow of as much as 200 pounds on one side or the other of the limb without damage to the player's joint. The principle upon which this invention is applied is the distribution of a sharp blow on the side of the limb near the joint to the muscles above and below the knee of elbow joint so as to divert the blow chiefly from the joint bone and cartilage structure. This is referred to as shock absorption.

One of the advantages of this invention is that it is very light in weight and yet sufficiently strong to produce the desired results. Conventional wrapping procedures are simple and rapidly done by the wearers themselves.

Other objects and advantages of the present invention will be apparent from the accompanying drawings and description, and the essential features will be set forth in the appended claims.

BRIEF DESCRIPTION OF THE DRAWINGS

In the drawings,

FIG. 1 is a top plan view of the first embodiment of this invention;

FIG. 2 is a view of the embodiment shown in FIG. 1 but with the rigid tongues bent with respect to the rocker connection member in a position corresponding to a bent limb position;

FIG. 3 is a sectional view enlarged taken along the line 3—3 of FIG. 2;

FIG. 4 is a top plan view of the rocker connection member and the pivotally attached tongues on opposite sides thereof in the same position as shown in FIG. 1;

FIG. 5 is an end elevational view taken along the line 5—5 of FIG. 1, this view being on the same scale as FIG. 3;

FIG. 6A is a fragmental plan view of the central portion of FIG. 6 showing an adjustment screw positioned to further limit the bending movement of a joint; while

DESCRIPTION OF THE PREFERRED EMBODIMENTS

Figure 6:
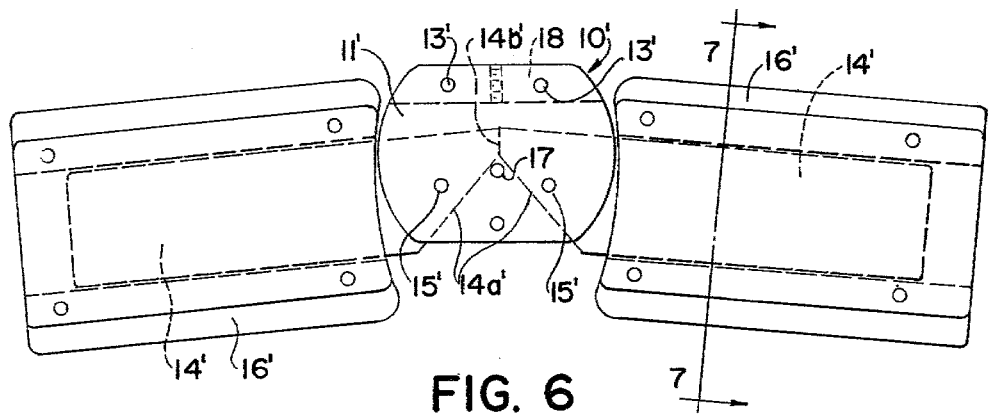
FIG. 6 is a top plan view of the rocker connection member with attached tongues as used in the second embodiment of this invention.

In the first embodiment of this invention, as shown in FIGS. 1-5, a rocker connection member 10 comprises parallel plates 11 spaced apart by central member 12, these three parts being held together ridigly by rivets 13, or in any other desired manner.

To the opposite sides of the rocker connection 10, there are attached three tongues 14, each having one end attached by rivets 15 to the rocker connection member 10. These tongues are linear and relatively rigid and are made of material having outstanding impact strength.

The pivotal connection between the tongues 14 and the rocker connection member 10 are so arranged that they permit substantially free bending of the limb joint normally but prevent reverse bending of the joint. This structure will be understood from a study of FIGS. 1, 2 and 4 of the drawings. Each tongue member is curved on one side as seen at 14a to provide a clearance so that the tongues may move from the straight line position of FIG. 1 to the bent position shown in FIG. 2. Also, the tongues have another end portion 14b which tightly engages the surfaces respectively shown at 12a, 12b, and 12c in FIG. 3 when the structure is in the straight line position of FIGS. 1 and 3. This prevents reverse bending of the joint. The step construction shown at 12a, 12b, and 12c provides flexibility in the sliding motions of the tongue members inside the surrounding sleeve so that the three tongue members can be seen inclined slightly in FIG. 2 to allow limb flexing without noticeable restriction.

A sleeve 16 surrounds each tongue member 14 on opposite sides of the rocker connection member. Each sleeve comprises a base sheet 16a which is bent as shown in FIG. 5 to generally conform to the surface of the human arm or leg. To the sheet 16a are rigidly connected two spacer members 16b which are spaced apart fairly closely to the tongue members 14 leaving just enough room for the tongue members to slide freely in the sleeve. Then a top flat member 16c is rigidly secured to the rest of the sleeve structure. It will be noted in FIGS. 1 and 2 that the spacing members 16b are a little wider apart at the end toward the rocker connection member than they are at the opposite end. This accommodates the movement of the three tongue members as they come from the straight position of FIG. 1 to the bent position of FIG. 2. Sleeves for FIG. 6 have parallel edges for the single wide tongue.

A suitable material for the construction of this invention, particularly the tongues 14, is a thermoplastic polycarbonate resin sold under the trademark LEXAN by General Electric Company. Under trade No. 101 and No. 141, this resin has an allowable dynamic stress at 73° F. between 15,000 and 20,000 p.s.i. It has a fatigue endurance over $10^5$ cycles. It has a specific gravity of 1.20 and has outstanding impact strength. In the embodiment described here, the tongues 14 are ¼ inch thick and ½ inch wide and six inches long. With this structure, one is assured the rupture of the protective device will take place first in rivet failure which will occur gradually and with almost a total absence of metal which is a prime requirement in this use of the device. Each of the protector units as shown in FIGS. 1 and 2 weighs less than one pound which assures no discomfort to the athlete wearing the same.

It should be understood that the device as shown in FIG. 1 is used by strapping the sleeves 16 on the leg of an athlete or patient, with one of the protectors on each side of leg, and fastening the same firmly in place by the use of tapes or similar procedures. This will place the rocker connection member 10 is position substantially opposite the hinge point of the knee joint. In one embodiment of the invention, the top plate of each sleeve 16c was made of LEXAN material just a little less than ⅛ inch thick. In testing, this device was subjected to a force of 200 pounds on the rocker 10 with sleeves 16 supported by blocks at right angles to the leg position which caused a slight deflection of the LEXAN material at the rocker 10 point, but, upon release of the pressure, the rocker connection returned to original position without permanent deformation.

The second embodiment of this invention is like that described in the first embodiment with the exception of the parts now to be described as seen in FIG. 6. Here the rocker connection member 10' is composed of two parallel plates 11' which are held rigidly in position properly spaced apart by spacer 18 and rivets 13'. Two linear rigid tongues or beams 14' are connected pivotally at 15' with the rocker connection 10' as shown. The tongues or beams 14' are cut away as shown at 14a' to permit the tongues 14' to bend toward each other downwardly as seen in FIG. 6 during a limb joint bending action. When the tongues 14' are turned from the bent position toward the generally straight position shown in FIG. 6, the flat end portions 14b' meet each other firmly as seen in FIG. 6. Also, at the same time a stop pin 17 may be fixed in the rocker connection member 10' to serve to limit the movement of the tongues 14' in a direction to prevent reverse bending of the joint to which the same is intended to be attached. The structure shown in FIG. 6 is supplied with a sleeve 16' surrounding each of the tongues 14' in the same manner as the sleeves 16 surround the tongues of the first embodiment, except that the side edges are parallel. This second embodiment is intended primarily for therapeutic and contact sports applications where very close, often unyielding, fit to a leg is wanted. When the sleeves and tongues are made to a close dimension, snugly fitting but free sliding maximum protection from a blow or push from in front or from the side is achieved. With the unit on each side of a joint, one pair of tongues may be reversed in bending direction to achieve a rigid stiff limb; that is, an open air cast. Note that the last mentioned feature tends to reduce normal yielding for muscle action. In knee rehabilitation, restriction often is exactly what is desired. In this form of the invention, longer beams or tongues 14' may be used to extend up or down the limb. However, as mentioned previously, this second embodiment may be built with extra looseness between the sleeves and the tongues sufficient to permit free longitudinal sliding movement of each tongue in its embracing sleeve while preventing twisting of said tongues in said sleeves about the pivotal connections with the rocker connection, so that this unit also could be used in regular football services and other contact sports. The same LEXAN was used in making the second embodiment with the tongues 14' being ¼ inch thick and 1½ inches wide.

It will be noted in FIG. 6 that the tongues 14' on opposite sides of the rocker connecting member are in the position for preventing reverse bending, and these tongues are so arranged that they are in less than true alinement, as in FIG. 1, by about 5° to 10°. This is accomplished by cutting the inner ends of tongues 14' at the proper angle along 14b' where they meet, or by proper positioning of the stop pin 17, or both.

Figure 6A:
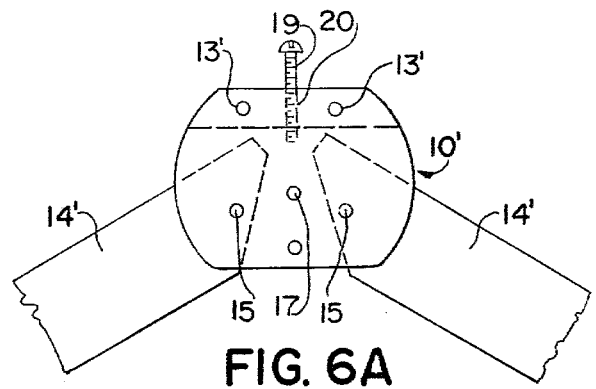
Figure 7:
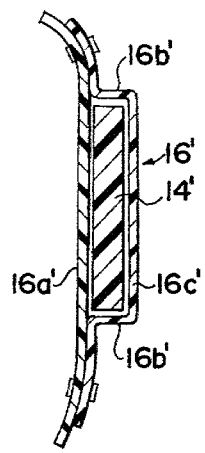
FIG. 7 is a sectional view taken along line 7—7 of FIG. 6.

Also shown in FIGS. 6 and 6A is a screw 19 passing through a threaded opening 20 in the rocker connection member in position to enter between the meeting inner ends of tongues 14', as seen in FIG. 6A to limit the bending movement of a limb, which is often necessary in therapy.

Not essential to the operation of this invention is the use of pads between the sleeves 16 or 16', and between the rocker connection member 10 or 10', and the body of the wearer. These pads could be strips of foam rubber or the like.

It is obvious that the sleeve 16' may be respectively positioned where desired relative to the knee joint, and the binding of sleeves 16' to the leg of the wearer may be as tight as is comfortable.

What is claimed is:

1. A knee joint protector consisting of a rocker connection member adapted for placement on one side of a human knee joint, two planar linear rigid tongues each about ¼ inch thick and about 1.50 inches wide and each pivotally connected at one end to said rocker connection member, the other end of one of said tongues in position to extend along a limb immediately above said knee joint, the other end of the other of said tongues in position to extend along a limb immediately below said knee joint, a separate rigid unitary sleeve having two open ends and surrounding each tongue sufficiently close to permit free longitudinal sliding movement of said tongues in said sleeves but to prevent twisting of said tongues in said sleeves about said pivotal connections, said sleeves adapted to be firmly attached to the limb in such positions at desired locations related respectively to the knee joint, and said tongues and said connections between said rocker connection member and said tongues permitting substantially free bending of the joint normally with compensating free sliding of said tongues in said sleeves but with portions engaging between said rocker connection and said tongues preventing reverse bending of the joint when said tongues on opposite sides of said rocker connection member are substantially in alinement.

2. A knee joint protector as defined in claim 1, wherein said connections between said rocker connection member and said tongues provides a clearance for such normal bending movement, and provides tightly engaging surfaces preventing opposite bending of the knee joint.

3. A knee joint protector as defined in claim 1, wherein said connections between said rocker connection member and said tongues provide a clearance for such normal bending movement, and provides a fixed pin in said rocker connection member preventing reverse bending of the joint.

4. A knee joint protector as defined in claim 1, wherein said tongues have at least four to five inches inside said sleeves which are open ended for longer tongues to extend.

5. A knee joint protector as defined in claim 1, wherein said tongues and said connections between said rocker connection member and said tongues are so arranged that in said position for preventing reverse bending said tongues on opposite sides of said rocker connecting member are in less than a true alinement position by about 5° to 10°.

6. Two knee joint protectors as defined in claim 1, each joint protector having a rocker connection member and two linear rigid tongues each pivotally connected at one end to said rocker connection member, and a separate rigid unitary sleeve surrounding each of said tongues sufficiently close to permit free longitudinal sliding movement of each tongue in its associated sleeve but to prevent twisting of said tongues in said sleeve about said pivotal connections, whereby said joint protectors may be assembled closely alongside opposite sides of a knee with said four sleeves tightly bound to the leg, thus permitting substantially free bending of said knee joint normally with compensating sliding of said tongues in their associated sleeves.

* * * * *